(12) United States Patent
Goodman et al.

(10) Patent No.: US 11,471,159 B2
(45) Date of Patent: Oct. 18, 2022

(54) FLEXIBLE MATERIAL DISPENSER

(71) Applicant: Ethicon, Inc., Somerville, NJ (US)

(72) Inventors: John Goodman, Ann Arbor, MI (US); Gregory Hake, Elk River, MN (US); Thomas Schoon, Maplewood, MN (US)

(73) Assignee: Ethicon, Inc., Raritan, NJ (US)

( * ) Notice: Subject to any disclaimer, the term of this patent is extended or adjusted under 35 U.S.C. 154(b) by 0 days.

(21) Appl. No.: 16/907,896

(22) Filed: Jun. 22, 2020

(65) Prior Publication Data

US 2020/0315624 A1  Oct. 8, 2020

Related U.S. Application Data

(60) Continuation of application No. 16/288,434, filed on Feb. 28, 2019, now Pat. No. 10,687,816, which is a
(Continued)

(51) Int. Cl.
*A61B 17/08* (2006.01)
*B65H 37/00* (2006.01)
*A61B 17/10* (2006.01)

(52) U.S. Cl.
CPC ............ *A61B 17/085* (2013.01); *A61B 17/10* (2013.01); *B65H 37/007* (2013.01); *Y10T 156/1348* (2015.01)

(58) Field of Classification Search
CPC ................ B65H 37/007; A61B 17/085; Y10T 156/1348
(Continued)

(56) References Cited

U.S. PATENT DOCUMENTS 2,845,041 A * 7/1958 Karn .................... B65H 37/007
118/257
4,080,348 A   3/1978 Korpman
(Continued)

FOREIGN PATENT DOCUMENTS

AU       52512/90       10/1990
AU        628179        9/1992
(Continued)

OTHER PUBLICATIONS

Parvizi, D. et al. 'Use of 2-Octyl Cyanoacrylate Together with a Self-Adhering Mesh (Dermabond™ Prineo™) for Skin Closure Following Abdominoplasty: An Open, Prospective, Controlled, Randomized, Clinical Study' Aesth Plast Surg (2013) 37 pp. 529-537.
(Continued)

*Primary Examiner* — James D Sells

(57) ABSTRACT

A dispensing device configured to operate with an adhesive backed mesh and backing film for tissue bonding is disclosed. The dispensing device provides for low-friction, low force pay-out of a desired length of an adhesive backed mesh to a wound site. The device prevents or eliminates distortion of the mesh prior to application to the wound site, and includes means for reducing or eliminating binding during use. The dispensing device is configured to operate in a "forward" mode (substrate to which mesh is applied passes beneath applicator after mesh is applied) to provide essentially an unobstructed view of the wound site during use.

1 Claim, 5 Drawing Sheets

Related U.S. Application Data continuation of application No. 15/711,293, filed on Sep. 21, 2017, now Pat. No. 10,258,335, which is a continuation of application No. 13/079,848, filed on Apr. 5, 2011, now Pat. No. 9,801,632, which is a division of application No. 11/759,774, filed on Jun. 7, 2007, now abandoned.

(58) Field of Classification Search
USPC .......................................................... 156/486
See application file for complete search history.

(56) References Cited

U.S. PATENT DOCUMENTS

| | | | |
|---|---|---|---|
| 4,094,250 A | 6/1978 | Theurer | |
| 4,447,482 A | 5/1984 | Heinzelman et al. | |
| 4,584,355 A | 4/1986 | Blizzard et al. | |
| 4,585,836 A | 4/1986 | Homan et al. | |
| 4,591,622 A | 5/1986 | Blizzard et al. | |
| 4,655,767 A | 4/1987 | Woodard et al. | |
| 4,718,971 A | 1/1988 | Summers | |
| 4,793,887 A | 12/1988 | Card et al. | |
| 4,793,888 A | 12/1988 | Card et al. | |
| 5,005,730 A | 4/1991 | Pickrell, Jr. et al. | |
| 5,164,444 A | 11/1992 | Bernard | |
| 5,178,717 A | 1/1993 | Rodriguez | |
| 5,232,958 A | 8/1993 | Mallya et al. | |
| 5,310,445 A | 5/1994 | Tucker | |
| 5,379,477 A * | 1/1995 | Tamai | B65H 37/007 15/104.94 |
| 5,383,900 A * | 1/1995 | Krantz | A61B 17/085 206/389 |
| 5,623,011 A | 4/1997 | Bernard | |
| 5,685,944 A * | 11/1997 | Nose | B65H 37/007 156/540 |
| 5,686,504 A | 11/1997 | Ang | |
| 5,705,551 A | 1/1998 | Sasaki et al. | |
| 5,707,482 A | 1/1998 | Fusselman | |
| 5,772,840 A | 6/1998 | Morinaga | |
| 5,851,347 A | 12/1998 | Rodriguez | |
| 5,851,348 A | 12/1998 | Muenzer et al. | |
| 5,928,611 A | 7/1999 | Leung | |
| 5,947,917 A | 9/1999 | Carte et al. | |
| 6,213,343 B1 * | 4/2001 | Damikolas | A61F 15/002 221/25 |
| 6,382,291 B2 | 5/2002 | Ronalds | |
| 6,453,968 B1 | 9/2002 | Hsu | |
| 6,521,045 B1 | 2/2003 | Koyama et al. | |
| 6,620,846 B1 | 9/2003 | Jonn et al. | |
| 6,755,321 B2 | 6/2004 | Solovay et al. | |
| 6,808,565 B1 | 10/2004 | Koyama et al. | |
| 7,094,250 B2 | 8/2006 | Stenton | |
| 9,801,632 B2 * | 10/2017 | Goodman | B65H 37/007 |
| 10,258,335 B2 * | 4/2019 | Goodman | A61B 17/10 |
| 10,687,816 B2 * | 6/2020 | Goodman | B65H 37/007 |
| 2002/0037310 A1 | 3/2002 | Jonn et al. | |
| 2004/0120849 A1 | 6/2004 | Stewart et al. | |
| 2005/0025559 A1 | 2/2005 | Stenton | |
| 2005/0178507 A1 * | 8/2005 | Hajny | B65H 37/007 156/538 |
| 2005/0182443 A1 | 8/2005 | Jonn et al. | |
| 2005/0234485 A1 | 10/2005 | Seegert et al. | |
| 2005/0274453 A1 | 12/2005 | Anvar | |
| 2006/0009099 A1 * | 1/2006 | Jonn | A61L 15/58 442/43 |
| 2009/0270884 A1 | 10/2009 | Hake | |

FOREIGN PATENT DOCUMENTS

| | | |
|---|---|---|
| DE | 102005034007 | 5/2006 |
| EP | 0719723 | 7/1996 |
| GB | 1009607 | 11/1965 |
| GB | 2078763 | 1/1982 |
| JP | 02-142095 | 11/1990 |
| JP | 02-146090 | 12/1990 |
| JP | 09-104562 | 4/1997 |
| WO | WO 94/15788 | 7/1994 |

OTHER PUBLICATIONS

International Preliminary Report on Patentability re: PCT/US2008/066107 dated Dec. 7, 2009.

International Search Report re: PCT/US2008/066107 dated Oct. 8, 2008.

Japanese Office Action for JP Patent Application No. 2010-511361 dated Dec. 25, 2013.

Text of First Office Action that issued in the corresponding Chinese Patent Application No. 200880019048.X.

\* cited by examiner

FLEXIBLE MATERIAL DISPENSER

CROSS REFERENCE TO RELATED APPLICATION

This application is a continuation of U.S. patent application Ser. No. 16/288,434 filed Feb. 28, 2019, which is a continuation of U.S. patent application Ser. No. 15/711,293 filed Sep. 21, 2017, now U.S. Pat. No. 10,258,335, which is a continuation of U.S. patent application Ser. No. 13/079,848 filed Apr. 5, 2011, now U.S. Pat. No. 9,801,632, which is a divisional of U.S. application Ser. No. 11/759,774 filed Jun. 7, 20027. The complete disclosures of the aforementioned related U.S. patent application is hereby incorporated herein by reference for all purposes.

FIELD

The present invention relates to a dispenser device for applying/dispensing a mesh.

BACKGROUND

Presently, patients undergoing surgical procedures requiring long incisions may require their incisions to be closed using sutures, staples, and/or adhesive strips. All of these closing methodologies may have difficulties, to varying degrees, with patient comfort, speed (for the clinician), clinical outcome (suture related infection/irritation), recovery time and cosmesis.

Skin closure strips, such as conventional adhesive bandages, are utilized for closure of relatively superficial skin wounds. However, the contact adhesives that are used with such strips typically retain adhesion for no more than a day or two and can lose adhesion quickly in the presence of moisture, for example, perspiration.

While improved materials and methods for wound approximation are generally known, for example, co-assigned U.S. Patent Application Publication No. 2006/0009099, these improved materials may be more generally accepted and more widely used if dispensing devices adapted to the unique characteristics of these materials were available. Therefore, a need continues to exist for devices and methods for dispensing materials useful in wound approximation and tissue bonding to provide a wider range of applications for these materials, from external to internal use, and from essentially non-biodegradable (where the materials are removed from the application site) to biodegradable (where the materials are not directly removed from the application site and degrade over time).

SUMMARY

Devices and methods for dispensing materials useful in wound approximation and tissue bonding are provided. The device is adapted to characteristics of the materials used in wound approximation and tissue bonding. Methods of tissue bonding using the device are also provided.

In an embodiment, a mesh dispensing device is provided. The device comprises a housing having an opening. A supply spool is rotatably mounted in the housing, the supply spool comprising a spool of mesh and backing film, the mesh comprising an adhesive substance applied over at least a portion of a side of the mesh, and the backing film detachably adhered to the adhesive substance. At least one guide element is mounted in the housing receiving the mesh and the backing film from the supply spool, such that the adhesive side of the mesh is presented at the opening of the housing. A take-up spool is rotatably mounted in the housing, the take-up spool rotatably coupled with the supply spool for receiving the backing film. Means for reducing or eliminating binding or slack of the detached backing film as the mesh is dispensed are provided.

In another embodiment, a method for dispensing a mesh for tissue bonding is provided. The method comprises providing a spool of mesh comprising a pressure sensitive adhesive applied over at least a portion of a side of the mesh, a polymerization initiator disposed in or on the mesh, and a backing film detachably adhered to the pressure sensitive adhesive. A dispensing device is provided, the dispensing device comprising a housing having an opening, the housing further comprising a pair of parallel projections at the opening. A supply spool is rotatably mounted in the housing receiving the spool of mesh and the backing film. A set of guide elements, where at least one guide element of the set of guide elements is rotatably mounted on the pair of projections and cooperatively receives the mesh and backing film from the supply spool and presents the pressure sensitive adhesive side of the mesh at the opening of the housing. A take-up spool is rotatably mounted in the housing, the take-up spool rotatably coupled with the supply spool for receiving the backing film from the set of guide elements. Means for reducing or eliminating binding or slack of the detached backing film are provided. A tissue surface is contacted with at least a portion of the pressure sensitive adhesive side of mesh presented by at least one of the set of guide elements. A portion of the pressure sensitive adhesive side of the mesh is adhered to the tissue surface. The dispensing device is operated in a forward direction by pushing or pulling the device along the tissue surface such that the adhered mesh drives the take-up spool with separation of the backing film at the set of guide elements. The mesh from the dispensing device is dispensed.

In another embodiment, a method for tissue bonding is provided. The method comprises providing a tissue surface in need of bonding. A dispensing device is provided comprising a housing having an opening, the housing further comprising a pair of parallel projections at the opening. A supply spool is rotatably mounted in the housing, the supply spool comprising a spool of mesh and backing film, the mesh comprising a pressure sensitive adhesive applied over at least a portion of a side of the mesh, and a backing film detachably adhered to the pressure sensitive adhesive. A set of guide elements, where at least one guide element of the set of guide elements is rotatably mounted on the pair of projections cooperatively receives the mesh and the backing film from the supply spool and presents the pressure sensitive adhesive side of the mesh at the opening of the housing. A take-up spool is rotatably mounted in the housing, the take-up spool rotatably coupled with the supply spool for receiving the backing film from the set of guide elements. Means for reducing or eliminating binding or slack of the detached backing film are provided. The tissue surface is contacted, where at least a portion of the pressure sensitive adhesive side of the mesh is positioned between the tissue surface and at least one of the set of guide elements. At least a portion of the pressure sensitive adhesive side of the mesh is adhered with the tissue surface. The mesh is dispensed from the opening of the dispensing device by operating the dispensing device in a forward direction along the tissue surface.

In another embodiment, a kit comprising the mesh dispensing device as described above and a polymerizable adhesive composition is provided.

The dispensing device herein disclosed may be used to dispense a material suitable for bonding a variety of tissue ranging from hard tissue (such as bone) to soft tissue (such as skin, organs, mucous membranes, and the like). The tissue can be either internal or external.

DETAILED DESCRIPTION

Figure 1A:
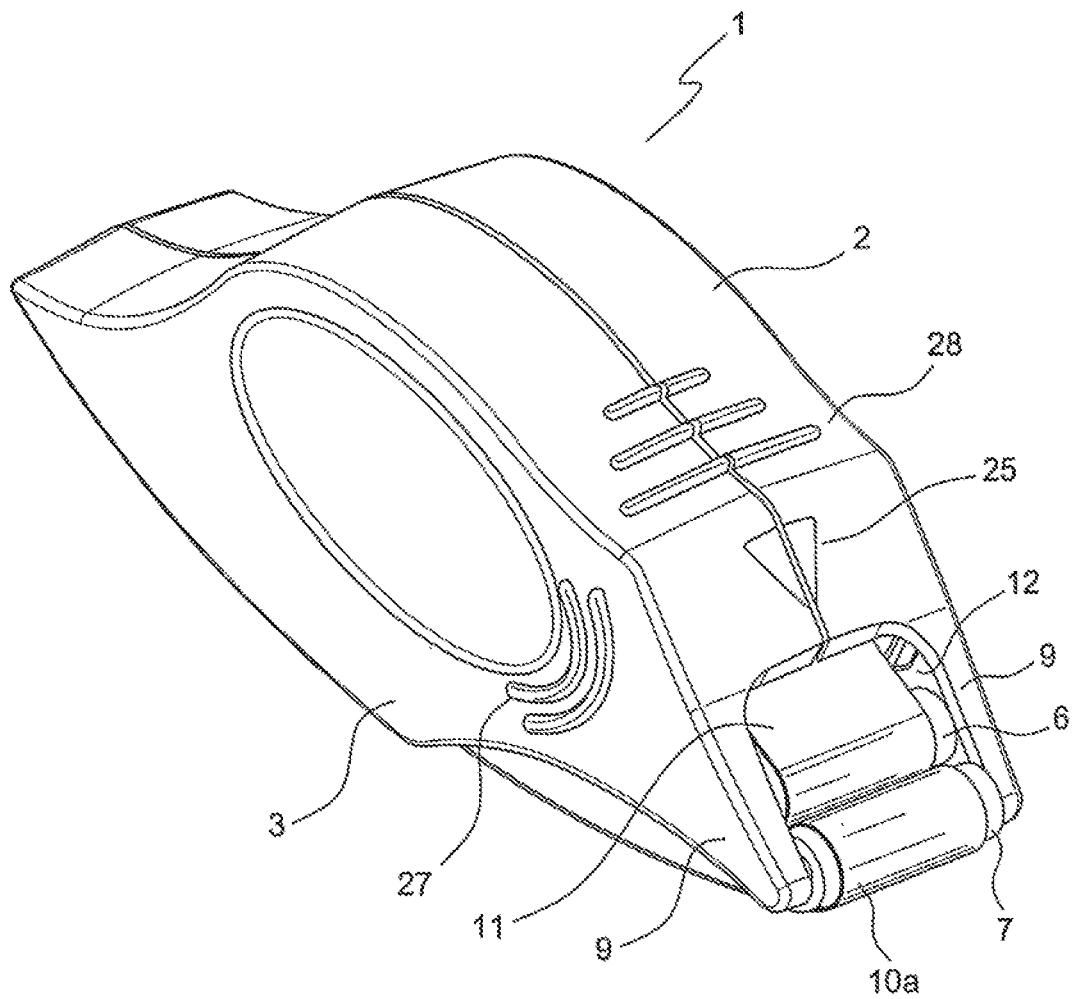
FIGS. 1A and 1B are a perspective views of dispenser embodiments herein disclosed.

Devices and methods for dispensing materials useful in wound approximation and tissue bonding are provided. The device is adapted to characteristics of the materials used in wound approximation and tissue bonding, in particular, components of composite products used in tissue bonding.

Composite products comprised of a tissue bonding material, such as an adhesive backed mesh, for example, used in conjunction with a polymerizable adhesive composition may be used for tissue bonding. Use of the aforementioned material requires that the mesh be adhered to a substrate, for example a patient's skin or tissue, straddling well-approximated wound edges. The polymerizable adhesive composition, for example, a cyanoacrylate (CA) adhesive may then be applied over the mesh after it is applied to a patient, further securing the mesh in place and promoting wound closure. The adhesive backed mesh holds the wound edges in place prior to application of the CA adhesive, and may provide a matrix for supporting initiating chemicals that modulate the curing rate of the CA adhesive and may also provide mechanical reinforcement of the CA adhesive.

To work effectively, the adhesive backed mesh preferably should be in intimate contact with the patient's skin over its entire surface. "Tenting" of the mesh (e.g., air gaps between the patient's skin and the mesh) may result in gaps that do not fill-in when the CA adhesive is applied, resulting in a discontinuous closure and/or area of weak adhesion, which may lead to premature separation of the incision. Furthermore, the surface to which the mesh is being applied may be undulating in its topography (e.g., being curved in 3-dimensions). To address these requirements, the adhesive backed mesh is typically flexible and compliant.

The adhesive backed mesh, which may be provided in the form of a strip, preferably should be precisely applied to the patient's skin such that the wound line is centered along the axis of the mesh strip as to evenly distribute the load on either side of the wound after completing application of the mesh strip (for approximating opposite sides of the wound line, for example). Lastly, the adhesive backed mesh preferably should hold the wound edges in alignment prior to application of the CA adhesive to ensure a desirable cosmetic outcome.

Collectively, the aforementioned attributes of an adhesive backed mesh provided in simple strip form may make it impractical to provide adequate tissue bonding in certain situations. There may be too many control points for the clinician to manage in order to provide an optimal deployment of the mesh, for example, where wounds are quite long (e.g., circumscribing a patient's entire body).

In addressing the aforementioned, a dispensing device configured to operate with an adhesive backed mesh and backing film for tissue bonding is provided. The dispensing device provides for low-friction pay-out of a desired length of the adhesive backed mesh. The device minimizes, prevents, or eliminates distortion of the mesh prior to application to the wound site, and reduces or eliminates binding during use. Moreover, the dispensing device herein disclosed is configured to operate with one hand in a "forward" mode or direction to provide essentially an unobstructed view of the wound site during use. By means of the "forward" mode or direction, the adhesive side of the mesh is dispensed and presented via passing beneath the device. For example, the mesh is applied to a longitudinal wound starting at a region proximal to the dispenser and moving the dispenser along the longitudinal dimension of the wound towards a distal region. The mesh is dispensed by passing under the dispenser leaving an applied mesh on the wound site starting at the proximal region and extending towards the distal region such that the view of the distal portion of the wound is substantially unobstructed by the dispenser as it is moved along the longitudinal dimension of the wound. Such mode of operation may provide for improved surgical and clinical application of the aforementioned composite tissue bonding products.

The dispenser herein disclosed provides for the surface of the adhesive backed mesh, which ultimately adheres to the substrate to which it is being applied, being oriented toward a backing film. Moreover, the dispenser herein disclosed reduces or eliminates the tensile load required to pay the tape from the dispenser, which may otherwise result in the mesh distorting and/or elongating and may lead to undesirable tenting of the mesh, for example. For similar reasons, the dispenser avoids highly frictional operated clutching mechanisms used to control binding and slack used in conventional dispensing devices that otherwise may distort or elongate the adhesive backed mesh. Additionally, the dispensing device herein disclosed is operable in a "forward" mode allowing visualization of the substrate immediately ahead of where the mesh is to be applied. Such a mode of operation may be ideal for a surgical setting where the clinician may need to follow an irregularly-shaped wound that may traverse over undulating contour. Such advantages are not collectively addressed in dispensers designed for conventional adhesive tape and other materials not directed to use in tissue bonding.

The device herein disclosed is adapted for use with materials that can be applied to a surface, and impregnated with a polymerizable adhesive composition, which upon setting or curing provides an adherent structure over the surface. For example, any adhesive backed mesh (or adhesive backed flexible material) suitable for use in the dispenser disclosed herein includes materials suitable for tissue bonding. Suitable flexible materials include, for example, those described in co-assigned U.S. Patent Application Publication No. 2006/0009099, incorporated herein by reference in its entirety. The mesh is preferably flexible or compliant, to allow the mesh to be placed on the desired surface (such as skin, organ, tissue, or the like) in a manner that allows the mesh to conform to the topology of the desired surface. Likewise, the mesh is preferably porous, to allow a subsequently applied polymerizable adhesive composition to pass through or permeate through the mesh and to polymerize, while adhering the mesh to the desired surface. A flexible material such as a film or tape may also be dispensed in the dispenser described herein instead of a mesh.

Preferably, the mesh comprises an adhesive substance on all or part of one side of the mesh. The strength of the adhesive substance on a lower surface of the mesh is such as to hold the mesh in position on the patient until the polymerizable adhesive composition may be applied.

A device for dispensing a mesh for purposes of tissue bonding is provided. Using the device as herein disclosed, application of the mesh is achieved without distortion of the mesh, allowing conforming to undulating/curved topography. Using the device as herein disclosed, application of the mesh may be achieved without compromise of the clinician's visualization of the wound edge during application.

The device herein disclosed allows for a one-handed mesh placement operation adaptable to long pieces of an adhesive backed mesh. The device may allow use of gloved hands and for the user to more accurately approximate a wound edge, for example, over an undulating path with minimal distortion to the mesh while providing clear visualization of the target trajectory.

The mesh dispenser as herein disclosed generally comprises a housing. The housing comprises a rear end, a front end, and an opening at the front end, a spool of mesh and backing film, a supply spool and take-up spool, the supply spool and take-up spool rotatably coupled, at least one guide element, and means for reducing or eliminating binding or slack of the backing film.

The housing of the dispenser herein disclosed may be constructed of plastic, metal, or combinations thereof. The housing may include segments that are secured together. The segments of the housing may be secured during assembly by fastening means. The segments may be reversibly secured by securing the segments together such as by a hinge or latch for replacing and/or assembling the components of the dispenser. The segments may contain receiving elements cooperatively positioned for the accepting and/or mounting of components, such as for example, axles for spools and/or guide elements.

The housing may include one or more forward projections at the opening that provide for mounting one or more guide elements that facilitate the dispensing, contacting, and/or adhesion of the mesh to the wound site. The projections may include a pair of parallel positioned arms adapted to mount one or more guide elements, such as for example, one or more guide rollers.

The mesh dispenser as herein disclosed comprises a take-up spool and a supply spool rotatably mounted within the housing. The take-up and supply spools may be constructed of plastic, metal, or combinations thereof. The take-up and supply spools are sized such that they are received by corresponding take-up/supply mounting axles, the axles being mounted on the inside of the housing so that the take-up and supply spools may rotate thereon. The take-up spool may comprise a sleeve having a slit or gap (e.g., a "c-sleeve") about its outer diameter for receiving the backing film between the sleeve and the take-up spool. The take-up spool and the supply spool may comprise an annular track for cooperatively accepting clutch means, such as an elastomeric belt.

The take-up and supply spools are rotatably coupled to each other to provide opposite unidirectional rotation such that the take-up and supply spools cooperatively function to release the mesh with attached backing film and to accept the detached backing film during use. The take-up and supply spools may be rotatably coupled, for example, with spur gears or frictionally engaged members. One or more pawls, in cooperative relation with one or both of the spur gears, for example, may be used to prevent reverse rotation of the spools.

As material pays off the supply spool and accumulates on the take-up spool the diameter of the two spools will change, increasing the surface velocity of the take-up spool and decreasing the surface velocity of the supply spool. This will cause a condition where the take-up spool will accumulate material at an increasing rate, eventually removing any slack in the system, which may cause the take-up and supply spools to bind. For clinical applications requiring short lengths of mesh, the initial take-up and supply spool diameters and gear ratios may be adjusted so that the mesh and backing film supply is exhausted before slack is initially created and before the spool diameters/gear ratios transition (from pay out and accumulation) such that the slack is consumed. However, for clinical applications requiring long lengths of mesh to be applied to a wound site, this approach is not feasible because of binding.

In view of the aforementioned binding, the rotatably coupled take-up and supply spools may independently include means for reducing or eliminating binding or slack in dispensing of long lengths of the mesh in the normal operation of the mesh dispenser. The means provided avoid the undesirable event of slack material or backing film accumulating in the applicator or tightening and/or binding resulting from the effectively changing diameters of the spools resulting from mesh and backing film depletion from the supply spool and backing film build-up on the take-up spool.

Means for reducing or eliminating binding or slack in dispensing of the mesh in the normal operation of the mesh dispenser independently include, for example, slip clutch elements or backing film tensioners. The clutch element may comprise a frictional member. In some embodiments, the clutch is used in combination with spool diameters and/or gear ratios such that the surface velocity of the take-up spool is greater than the surface velocity of the supply spool. In such a configuration, build up of backing film slack and binding of the backing film is reduced or eliminated.

The clutch element may comprise a sleeve and a frictional member providing an interference fit between the sleeve and the take-up or the supply spool. The friction member may be an o-ring, for example. The sleeve comprises a sleeve inner diameter sized to be received by the take-up spool or the supply spool. The frictional member may be positioned between the sleeve and the supply spool or the take up spool. The frictional member may be positioned using a counterbore at either end of the spool or sleeve. The dimensioning of outer diameters of the take-up or supply spool, the inner diameter of the sleeve, and the thickness of the frictional member may be adjusted such that there is an interference fit in an assembled state. This configuration provides a slip clutch coupling between the sleeve and spool. A frictional member may include a surface element incorporated on the sleeve or the spool or a surface treatment of the sleeve or spool.

The amount of interference between the sleeve or the spool and the frictional member may be adjusted to provide a target amount of force such that slack is removed while not causing distortion of the mesh and/or that binding is prevented or eliminated during use. In embodiments, the amount of force required to cause the aforementioned clutch element to slip may be adjusted to be less than the force needed to distort the mesh. This may be between about 0 lb to about 1 lb, and may preferably be between about 0.4 lb to about 0.6 lb.

A tensioner for reducing or eliminating binding or slack during normal use of the mesh dispenser may be used. The tensioner may include a cooperatively joined spring and lever assembly mounted within the housing. The tensioner may be used independently or in combination with the clutch elements. The spring and lever assembly is preferably coupled with a guide roller accepting the backing film. The tensioner, for example may comprise a spring secured to the housing at one end of the spring and a lever, the lever pivotally secured to the housing at one end of the lever. A tensioning element may be secured to an opposite end of the spring and an opposite end of the lever, the tensioning element positioned such that the take-up spool is between the tensioning element and the opening in the housing, the tensioning element receiving the backing film prior to the take-up spool. The axial load of the spring and lever tensioner may be selected to optimize the detachment of the backing film from the mesh. The tensioner may be an assembly comprising a spring and lever, each positioned within the housing and pivotably coupled to a tensioning element. The tensioning element positioned such that the take-up spool is between the opening of the housing and the tensioning element. The backing film traverses around the tensioning element prior to being received by the take-up spool so as to provide tension control and/or remove slack from the routing of the backing film.

By way of example, slip clutch elements may include a take-up spool rotatably mounted within the housing, the take-up spool having a take-up spool outer diameter; a sleeve having a sleeve inner diameter; and an elastomeric o-ring providing an interference fit between the sleeve inner diameter and the take-up spool outer diameter.

Further by way of example, slip clutch elements may include a supply spool rotatably mounted within the housing, the supply spool having a supply spool outer diameter; and a sleeve having an inner diameter; and an elastomeric o-ring providing an interference fit between the sleeve inner diameter and the supply spool outer diameter.

Further by way of example, a tensioner assembly may be used. The tensioner assembly may comprise a spring and lever, each positioned within the housing and pivotably coupled to a tensioning element, the tensioning element positioned rearward of the take-up spool in the housing such that the backing film traverses around the tensioning element prior to being received by the take-up spool so as to provide tension to the backing film.

Further by way of example, an elastic drive belt rotatably coupling the take-up spool and supply spool, the elastic belt providing slippage of the take-up spool, may be provided.

The sleeve of either the take-up spool or the supply spool may contain means for receiving clutch elements. For example, the sleeve may contain an annular groove in its inner diameter for receiving clutch elements. The outer diameter of either sleeve may be adjusted to optimize the ratio of take-up/supply spool diameters.

The mesh dispenser as herein disclosed comprises one or more guide elements mounted within the housing and/or mounted at the opening of the housing. Guide elements provide, in part, that the mesh and backing film or the detached backing film pass through the device in a controlled manner and do not inadvertently become tangled or jammed from slack in the mesh and backing film during assembly or use. The guide elements may be constructed of plastic, metal, or combinations thereof. For example, the guide elements may be teflon, polyethylene, ultra-high molecular weight polyethylene or stainless steel. Preferably, the guide elements have a low surface friction such that facile traversing of the detached mesh, detached backing film, or mesh and backing film over the guide element surface is provided. When passing over the guide elements, the adhesive side of the mesh is oriented away from the guide elements so as to prevent or eliminate adhesion of the mesh to the guide elements. Thus, it is preferable that the guide elements are constructed or coated with a material with poor adhesion to the adhesive substance such that the adhesive substance on the mesh does not adhere to the guide element, compromising subsequent operation of the device. In embodiments, the guide elements are made of polyethylene.

The guide elements may independently be rotatably mounted on axles within the housing, at the opening of the housing, or between the projections from the housing. The rotatably attached guide elements may be received by guide axles, the guide axles fixedly mounted within the housing or at the opening, or fixedly mounted between the projections of the housing. The guide elements may independently be fixedly mounted in the housing, at the opening, or between the projections from the housing provided that the surface of the guide elements is of low friction. Low surface friction may include the application of lubricants suitable for use in medical applications on the surface of the guide elements.

The guide elements may comprise one or more set of elements in close proximity to each other. The guide elements may comprise a set of guide elements that receive the mesh and backing film from the supply spool and facilitate the detachment of the backing film from the mesh. Guide elements may provide for presenting adhesive side of the mesh to the wound site and pressing the mesh down on the wound site for promoting adhesion of the mesh to the patient. In embodiments, the guide elements are cylindrical in shape, such as, for example, rollers.

At least one guide roller may be positioned at the opening of the housing, for example, between the ends of the projections from the housing. A set of guide rollers may be positioned at the opening or between the ends of the projections from the housing. The set of guide rollers may be used with one or more rollers within the housing to provide control of the detached backing film. The set of rollers may be in close proximity to each other, such that the set of rollers assists in detaching the backing film from the mesh in close proximity to the tissue or wound site. Given the flexible nature of the mesh, it may be desirable that the length of unsupported mesh (mesh length after separation from the backing film), until application to the patient, be minimized. The axial loads required to feed the mesh and backing film through the mesh dispenser may cause the mesh to distort, for example, stretching in length while simultaneously shrinking in width. For example, non-optimal conditions may exist when using the mesh dispenser herein disclosed, such as a wet field (blood, saline, or other body fluids), or a highly tortuous path-type wound site. The force of the mesh trying to recover from a distorted shape to its original shape may cause the mesh to pull loose from the patient, requiring the clinician to either replace or reposition the mesh. The amount of distortion in the mesh may increase with unsupported length. By positioning guide elements as close as possible to the point of application to the patient, unsupported length may be minimized. Small diameter guide elements may be used to provide for an increased release angle between the mesh and backing film, which may minimize the force required to separate the mesh from backing film.

Preferably, a set of two guide rollers are positioned at the opening, for example, between the ends of the projections from the housing, which would provide for one of the set of guide rollers being in contact with the tissue or wound site during normal operation of the mesh dispensing device. In this configuration, one of the set of guide rollers may independently assist in the adhesion of the mesh to the wound site, assist in wound approximation, and assist in the forward motion of the device along the wound line. In embodiments, the set of guide rollers positioned between the ends of the projections from the housing are used in combination with one or more guide rollers positioned within the housing for controlling the mesh and backing film and detached backing film. Other guide elements located within the housing may be used to prevent the mesh from coming in contact with the opening The mesh dispenser as herein disclosed comprises a spool of mesh and backing film rotatably loaded on or mounted in the supply spool. The mesh spool is sized to be received by the supply spool or supply spool sleeve. The mesh with backing film may be wound onto the supply spool. The spool of mesh and backing film may include the sleeve of the above described slip clutch, the sleeve sized to be rotatably loaded on the supply spool. Alternatively, the mesh with backing film may be provided on a roller and rotatably loaded on the supply spool. The amount of mesh on the spool may be adjusted to minimize the change in diameter of the supply and take-up spool during use. The supply spool may contain an adequate amount of mesh and backing film as needed for the target clinical application.

Adequate dead space is provided in the housing to allow backing film slack to build up due to the fact that the pay-out speed of the supply spool and take-up speed of the take-up spool decreases ((pay-out speed)/(take-up speed)$_{Time\ 0}$>(pay-out speed)/(take-up speed)$_{Time>0}$) as the spools rotate and the mesh is dispensed. Guiding rollers located within the housing are provided to route the detached backing film in such a manner as to ensure it does not become tangled in any of the device mechanisms. In embodiments, the take-up spool is coupled to its drive gear by a clutching mechanism. This mechanism keeps the liner paper tight so that slack in the device is reduced or eliminated. The device is configured such that the mesh is deployed to the tissue while pushing or pulling the dispenser forward. In this manner, the clinician is presented with a clear view of the wound line on the tissue and is able to provide that the mesh substantially remains centered about this wound line as it is being applied.

The mesh may be protected within the interior of the mesh dispenser until application is started. Means may also be provided to facilitate initial separation of the mesh from the backing film when applying the mesh to the patient. For example, a hand leader (e.g., a strip of plastic, paper, or other suitable material) may be attached to the beginning of the mesh at the outer-most wrap of the supply spool. The hand leader follows the mesh-dispensing path out of the dispenser and may be attached to the exterior of the housing segments during assembly and/or prior to use. The starting end of backing film at the outer-most wrap of the supply spool (corresponding with the hand leader) may be threaded through the guide elements of the device and may be attached to the take-up spool.

In use, the outer end of the hand leader is freed from the housing and pulled towards the rear of mesh dispenser. The hand leader initiates detachment of the mesh from the backing film and routes the detached mesh to the opening with the adhesive side of the mesh presented to tissue or wound site. The mesh dispenser herein disclosed is positioned at a wound site, for example, near the end or edge of the wound. A portion of mesh initially presented from the dispenser is adhered to the wound site via a PSA on the mesh starting at a region of the wound line proximal to the dispenser, and the mesh dispenser is then pushed or pulled along the wound line towards a distal region of the wound line so the mesh portion initially passes under and later behind the dispenser as the dispenser is moved from the proximal region of the wound line to the distal region of the wound line. Mesh and backing film are routed past guide rollers that may provide a separation point for the mesh and backing film in cooperation with the mesh adhering to the wound site, directing the mesh out of the device to the wound site as well as directing the backing film to the take-up spool where it is collected.

A method for dispensing a mesh for tissue bonding using the device herein disclosed is also provided. The method is particularly useful for dispensing a spool of mesh comprising a pressure sensitive adhesive applied over at least a portion of a bottom side of the mesh, a polymerization initiator disposed in or on the mesh, and a backing film detachably adhered to the pressure sensitive adhesive. In embodiments, the method comprises providing a dispensing device with a set of guide elements positioned at the opening of the housing, as herein disclosed. A tissue surface is contacted with the device, where at least a portion of the bottom side of mesh is positioned between the surface and at least one of the set of guide rollers of the device. At least a portion of the bottom side of the mesh is adhered with the tissue surface. The device is pushed or pulled in a forward direction along the tissue surface such that the adhered mesh provides rotation of the supply spool with separation of the backing film at the set of guide rollers to provide for dispensing the mesh from the dispensing device.

A method for tissue bonding using the device herein disclosed is also provided. The method comprises providing a tissue surface in need of bonding. The dispensing device is brought into contact with the tissue surface, where at least a portion of the bottom side of the mesh is positioned between the tissue surface and at least one of the set of guide elements of the device. At least a portion of the bottom side of the mesh is adhered with the tissue surface. The mesh is dispensed from the opening of the dispensing device by pushing or pulling the dispensing device in a forward direction along the tissue surface. In this manner, tissue edge approximation may be performed concurrent with controlled placement of the mesh.

The method may further comprise applying a polymerizable adhesive composition over and substantially covering at least a portion of the mesh; and allowing the polymerizable adhesive composition to permeate into and under the mesh and polymerize to form a composite structure bonded to the tissue surface.

The adhesive backed mesh used in the dispensing device herein disclosed may be porous. By "porous" is meant herein either that the bulk of the mesh has pores, such that the subsequently applied polymerizable adhesive composition is soaked up or absorbed by the bulk material, or that the bulk of the mesh has voids (like a net or screen), such that the subsequently applied polymerizable adhesive composition passes directly through the bulk material, with or without being soaked up or absorbed by the bulk material. For example, in the case of textile materials, "porous" is generally used to mean that the applied adhesive composition permeates and passes through interstices between the fibers, but does not necessarily pass into and through the fibers themselves.

Such porosity (or other properties such as hydrophobicity or hydrophilicity) will also allow a polymerization initiator or rate modifier to be loaded in or on the mesh prior to use, to initiate the subsequently applied polymerizable adhesive composition. Such porosity will also preferably allow air and fluid to pass through the mesh, either through pores per se, or through voids in the bulk material. Depending upon the degree of porosity and/or the size of the openings, such porosity of the mesh or ability of air and fluid to permeate through the mesh may be tailored either to remain after a final composite material is formed, or to be absent therefrom. The mesh is also preferably non-toxic, as it is intended to be used cover a wound, such as on biological tissues. As such, the mesh should be biologically compatible with the desired substrate (such as tissue, skin, organ, or the like), and is preferably a material that is governmentally approved or generally regarded as safe for the desired purpose. By way of example, suitable mesh materials are disclosed in United States Patent Applications 2006/0009099 and 2005/0182443, incorporated herein by reference in their entirety.

The mesh may be a textile or mesh/web material. Suitable textile materials may be formed of either synthetic or natural materials. Such textile material may be formed of either woven or non-woven fabrics or materials. The mesh may be, for example, any suitable polymeric film, plastic foam (including open celled foam), a woven fabric, knitted fabric, a non-woven fabric, mixture thereof, or the like. In particular, suitable mesh may thus be prepared, for example, from nylon, a polyolefin film, such as polyethylene, polypropylene, ethylene propylene copolymers, and ethylene butylene copolymers, polyurethanes, polyurethane foams, polystyrenes, plasticized polyvinylchlorides, polyesters, polyamides, polylactic acid, polyglycolic acid, polycaprolactone, copolymer mixtures of the above, and cotton. Suitable specific examples include, for example, nylon, polyethylene, polypropylene, ethylene propylene copolymers, ethylene butylene copolymers, polyurethane, polystyrene, plasticized polyvinylchloride, polyester, polyamide, cotton, polytetrafluoroethylene (PTFE), biovascular material, collagen, GoreTex®, DACRON®, etc.

The mesh may be formed of a synthetic, semi-synthetic, or natural organic material. Thus, for example, the mesh may be formed of a synthetic or natural polymer material, but not from a material such as metal (such as silver, steel or the like) or glass or ceramic. The mesh may be either biodegradable, or not biodegradable. The mesh is preferably resistant to tearing. The thickness of the mesh may be from about 0.1 mil to about 80 mils. In another embodiment, the thickness of the mesh is from about 0.5 mil to about 20 mils, preferably from about 0.7 mil to about 10 mils, or from about 1 mil to about 5 mils.

The mesh may be a strip from about 10 cm to about 80 cm, preferably from about 30 cm to about 60 cm in length. The mesh strip may be from about 0.1 cm to about 5 cm, preferably from about 1 cm to about 3 cm, more preferably 2 cm, in width.

The mesh may be selected to be elastic or have some memory effect. In such embodiments, the elastic properties of the mesh may desirably provide a degree of pressure or stress at the application site, for example, to maintain wound edge approximation. Likewise, in embodiments where such additional degree of pressure or stress at the application site is not desired, the mesh may be selected to have less or no elasticity.

The mesh may be either biodegradable, or not biodegradable. By "biodegradable" is meant that the mesh biodegrades over time in vivo, such that it does not require physical removal of the mesh after a set period of time. Thus, for example, a biodegradable mesh is one that, in the in vivo environment, will biodegrade over a period of from about one week to about five years. A non biodegradable material is one that does not biodegrade in an in vivo environment within about five years. Such a non biodegradable material thus would require physical removal of the mesh at a desired time, rather than slowly deteriorating over time.

The mesh of the mesh dispenser herein disclosed may contain materials such as a polymerization initiator, accelerator, rate-modifier, and/or cross-linking agent for initiating polymerization and/or cross-linking of a polymerizable monomer material. The mesh preferably includes one or more chemical materials located in or on the mesh. For example, one or more chemical substances may be dispersed in or on the mesh, such as being chemically bound, physically bound, absorbed, or adsorbed to the mesh. Thus, for example, the mesh preferably includes at least a polymerization initiator or rate modifier, and may optionally include one or more bioactive materials. As desired, the one or more chemical substances may be either immobilized in or on the mesh, for example, so that it has a desired effect but is not detached from the mesh during use.

For example, a polymerization initiator or rate modifier may be loaded in or on the mesh so that the initiator or rate modifier provides the desired initiation or rate modification effect to a subsequently applied polymerizable adhesive composition. The polymerization initiator or rate modifier may be immobilized in or on the mesh, so that the initiator or rate modifier does not become detached from the mesh and its residues dispersed in the resultant polymeric material. Alternatively, for example, the polymerization initiator or rate modifier may be initially attached to the mesh, but only in such a manner that it becomes mobilized or solubilized by a subsequently applied polymerizable adhesive composition and dispersed in the resultant polymeric material.

If desired, a combination of chemical substances may also be provided in or on the mesh, to provide multiple effects. For example, as described above, a first chemical species (such as a polymerization initiator or rate modifier) may be immobilized in or on the mesh, while a second, different chemical species (such as a bioactive material) may be detachably attached to the mesh. Other combinations of chemical species and resultant effects are also envisioned.

When present in or on the mesh, the chemical substances (i.e., polymerization initiator, rate modifier, and/or bioactive materials, or other additives), may be incorporated in or on the mesh in any suitable manner. For example, the chemical substance may be added to the mesh by contacting the mesh with a solution, mixture, or the like including the chemical substances. The chemical substance may be added to the mesh, for example, by dipping, spraying, roll coating, gravure coating, brushing, vapor deposition, or the like. Alternatively, the chemical substance may be incorporated into or onto the mesh during manufacture of the mesh, such as during molding, knitting/weaving, scouring, tenting, plaiting or other processing or the like of the mesh.

The chemical substance may be present in or on the mesh in any suitable concentration and manner. For example, the chemical substance may be applied in a uniform manner to the mesh, such that there is a substantially uniform concentration of the chemical substance across the mesh. Alternatively, the chemical substance may be applied such that a concentration gradient exists across or through the mesh. For example, a greater or smaller concentration of the chemical substance could exist at the center or edges of the mesh, or a greater or smaller concentration of the chemical substance could be applied on one side of the mesh as compared to an opposite side. Further, the chemical substance may be applied in a uniform manner to the mesh, or it may be applied in a non-uniform random or patterned manner (such as lines, dots, concentric circles, or the like). The chemical substances may also be on, beneath, or in the pressure sensitive adhesive layer applied to the mesh.

Other chemical substances that may be present in or on the mesh include, but are not limited to, any suitable and preferably compatible additive that enhances performance of the composite structure. Such additional chemical substances may be bioactive or non-bioactive. Suitable other chemical substances thus include, but are not limited to, colorants (such as inks, dyes and pigments), scents, protective coatings that do not chemically detach, temperature sensitive agents, drugs, wound-healing agents, anti-microbial agents and the like.

The polymerization initiator or rate modifier loaded in or on the mesh may provide a number of advantages for example, the tailoring of the setting or polymerization time of the applied polymerizable adhesive composition. For example, the type and/or concentration of initiator that is applied to the mesh may be selected so as to provide faster or slower polymerization time. The concentration of polymerization initiator or rate modifier may be increased to provide a faster polymerization time, or may be decreased to provide a slower polymerization time.

Because the polymerization initiator or rate modifier is loaded directly in or on the mesh, it is not necessary to mix the polymerizable adhesive composition with a polymerization initiator or rate modifier prior to application. This may allow a longer working time, where the polymerizable monomer composition may be more precisely and carefully applied over a longer period of time.

Such suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used.

Benzalkonium or benzyltrialkyl ammonium halides such as benzyltrialkyl ammonium chloride may be used. When used, the benzalkonium halide may be benzalkonium halide in its unpurified state, which comprises a mixture of varying chain-length compounds, or it can be any suitable purified compound including those having a chain length of from about 12 to about 18 carbon atoms, including but not limited to C12, C13, C14, C15, C16, C17, and C18 compounds. By way of example, the initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfite, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Mixtures of two or more, such as three, four, or more, initiators or accelerators may be used. A combination of multiple initiators or accelerators may be beneficial, for example, to tailor the initiator of the polymerizable monomer species. For example, where a blend of monomers is used, a blend of initiators may provide superior results to a single initiator. For example, the blend of initiators can provide one initiator that preferentially initiates one monomer, and a second initiator that preferentially initiates the other monomer, or can provide initiation rates to help ensure that both monomer species are initiated at equivalent, or desired non-equivalent, rates. In this manner, a blend of initiators can help minimize the amount of initiator necessary. Furthermore, a blend of initiators may enhance the polymerization reaction kinetics. The polymerization initiator, accelerator, rate-modifier, and/or cross-linking agent may be incorporated into the mesh using impregnation methods known in the art.

The adhesive substance used in the mesh may, for example, be any suitable adhesive substance. Preferably, the adhesive substance is a medical grade adhesive, such as acrylic based pressure sensitive adhesives (PSAs), rubber based pressure sensitive adhesives, silicone pressure sensitive adhesives, mixtures thereof, or the like. It is preferred that the adhesive substance be different from the polymerizable adhesive composition. Thus, for example, it is preferred that while the polymerizable adhesive composition can be, for example, a polymerizable monomeric adhesive composition, the adhesive substance is a material that is not a polymerizable adhesive composition, such as a pressure sensitive adhesive.

Suitable rubber based PSAs include, but are not limited to, those taught in U.S. Pat. No. 5,705,551 and in U.S. Pat. No. 4,080,348, the disclosures of which are hereby incorporated by reference. Examples of polymeric rubber bases include one or more of styrene-isoprene-styrene polymers, styrene-olefin-styrene polymers including styrene-ethylene/propylene-styrene polymers, polyisobutylene, styrene-butadiene-styrene polymers, polyisoprene, polybutadiene, natural rubber, silicone rubber, acrylonitrile rubber, nitrile rubber, polyurethane rubber, polyisobutylene rubber, butyl rubber, halobutyl rubber including bromobutyl rubber, butadiene-acrylonitrile rubber, polychloroprene, and styrene-butadiene rubber.

A particularly useful rubber based adhesive is that which has a thermoplastic elastomeric component and a resin component. The thermoplastic elastomeric component contains about 55-85 parts of a simple A-B block copolymer wherein the A-blocks are derived from styrene homologs and the B-blocks are derived from isoprene, and about 15-45 parts of a linear or radical A-B-A block copolymer wherein the A-blocks are derived from styrene or styrene homologs and the B-blocks are derived from conjugated dienes or lower alkenes, the A-blocks in the A-B block copolymer constituting about 10-18 percent by weight of the A-B copolymer and the total A-B and A-B-A copolymers containing about 20 percent or less styrene. The resin component consists of essentially of tackifier resins for the elastomeric component. In general any compatible conventional tackifier resin or mixture of such resins may be used. These include hydrocarbon resins, rosin and rosin derivatives, polyterpenes and other tackifiers. The adhesive substance may contain about 20-300 parts of the resin component per one hundred parts by weight of the thermoplastic elastomeric component. One such rubber based adhesive substance is commercially available from Ato Findley under the trade name HM3210.

Useful acrylic based PSAs include, but are not limited to, those taught in U.S. Pat. Nos. 5,947,917 and 5,164,444 (acrylic emulsion), U.S. Pat. No. 5,623,011 (tackified acrylic emulsion). It can also be radiation curable mixture of monomers with initiators and other ingredients such as those taught in U.S. Pat. No. 5,686,504 (UV cured acrylic) and U.S. Pat. No. 5,232,958 (EB cured). The disclosures of these patents are hereby incorporated by reference.

It is contemplated that any acrylic based polymer capable of forming an adhesive layer with sufficient tack to adhere to the mesh, the backing film or to a substrate, and with acceptable adhesion to skin, may be used. In certain embodiments, the acrylic polymers for the pressure-sensitive adhesive layers include those formed from polymerization of at least one alkyl acrylate monomer or methacrylate, an unsaturated carboxylic acid and optionally a vinyl lactam. Examples of suitable alkyl acrylate or methacrylate esters include, but are not limited to, butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate, and the like, and mixtures thereof. Examples of suitable ethylenically unsaturated carboxylic acids include, but are not limited to, acrylic acid, methacrylic acid, fumaric acid, itaconic acid, and the like, and mixtures thereof. A preferred ethylenically unsaturated carboxylic acid monomer is acrylic acid. Examples of suitable vinyl lactams include, but are not limited to, N-vinyl caprolactam, 1-vinyl-2-piperidone, 1-vinyl-5-methyl-2-pyrrolidone-, vinyl pyrrolidone, and the like, and mixtures thereof.

Useful silicone pressure sensitive adhesives include those commercially available from Dow Corning Corp., Medical Products and those available from General Electric. Examples of silicone adhesives available from Dow Corning include those sold under the trademarks BIO-PSA X7-3027, BIO-PSA X7-4919, BIO-PSA X7-2685, BIO-PSA X7-3122 and BIO-PSA X7-4502. Additional examples of silicone pressure sensitive adhesives are described in U.S. Pat. Nos. 4,591,622, 4,584,355, 4,585,836 and 4,655,767, the entire disclosures of which are incorporated herein by reference.

The adhesive substance may also include one or more tackifiers, plasticizers, antioxidants, cutting agents such as waxes, and surfactants. Other optional materials that may be added to the adhesive substance layer in minor amounts (typically less than about 25% by weight of the elastomeric phase) include pH controllers, medicaments, bactericides, growth factors, wound healing components such as collagen, antioxidants, deodorants, perfumes, antimicrobials and fungicides.

The backing film may be any suitable backing or release material used to cover the adhesive substances applied to the bottom side of the mesh. Such backing materials are well known in the art for covering pressure sensitive adhesives and can include, for example, paper, plastic, or the like. By way of example, the backing film may be a silicone treated material. Preferably, the backing film is of a material that prevents or eliminates the mesh from sticking to itself when it is wrapped around the supply spool. The backing film may substantially isolate most of the initiating chemical of the mesh from the PSA (on the bottom surface of the mesh) on adjoining layers of mesh and backing film when on the spool.

The method of tissue bonding herein disclosed includes a polymerizable adhesive composition applied over the mesh after the mesh is applied to a tissue or wound site. The polymerizable adhesive composition may comprise a polymerizable monomeric adhesive. In embodiments, the polymerizable adhesive composition comprises a polymerizable 1,1-disubstituted ethylene monomer formulation. In embodiments, the polymerizable adhesive composition comprises a cyanoacrylate formulation. In embodiments, synthetic polymerizable adhesive materials such as polyurethane, polyethylene glycol, acrylates, glutaraldehyde and biologically based adhesives may be used.

Suitable $\alpha$-cyanoacrylate monomers which may be used, alone or in combination, include alkyl $\alpha$-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other $\alpha$-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl $\alpha$-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

The mesh dispenser herein disclosed may be provided in a kit comprising additional components. The kit may comprise at least one mesh dispenser device as herein described, and one or more containers of polymerizable adhesive composition. The different components or groups of components may be sterilized in separate containers before packaging the components or groups of components within a kit, and thereafter sterilizing the kit as disclosed in co-assigned U.S. Pregrant Patent Publication No. 2004/0120849, incorporated herein by reference in its entirety. The kit may include one or more polymerizable adhesive compositions.

Figure 1B:
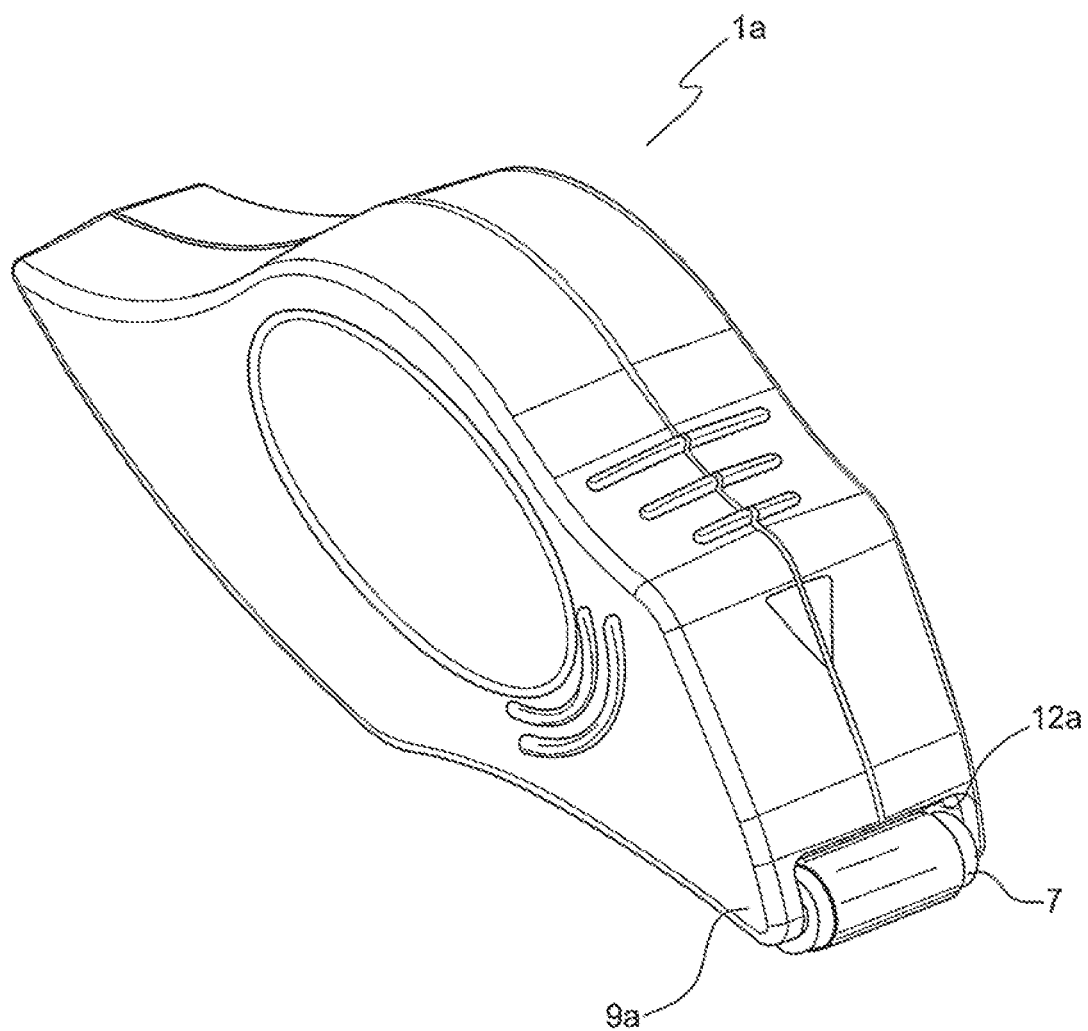
Figure 2:
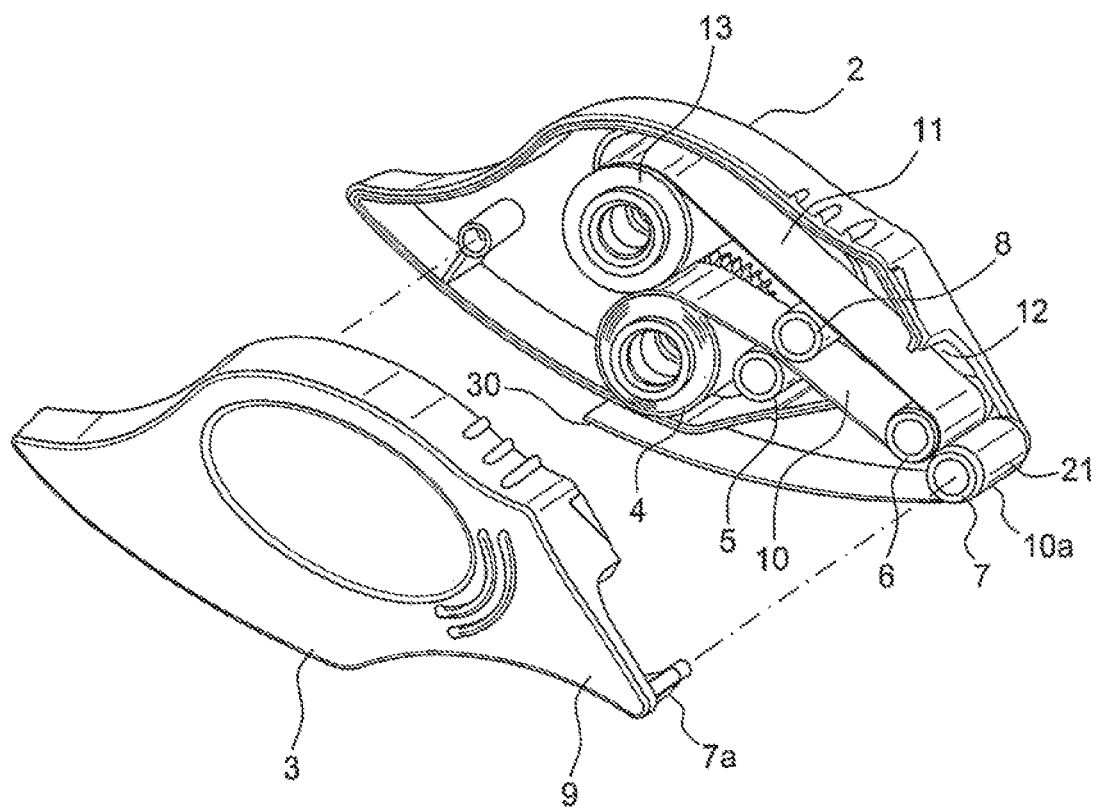
FIG. 2 is an exploded view showing various elements of a dispenser embodiment of FIG. 1.
Figure 3:
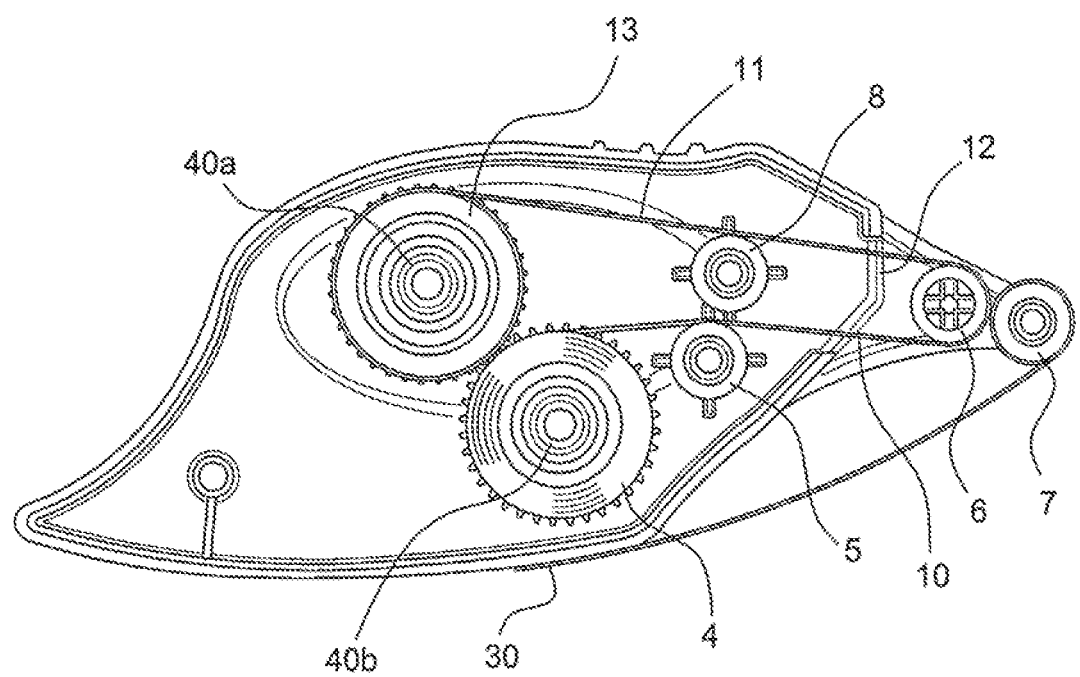
FIG. 3 is a plan view showing the assemblage of elements of the embodiment of FIG. 1.

Referring now to the Figures, FIGS. 1A and 1B are perspective views of embodiments of the mesh dispenser 1 and 1a, respectively, comprised of housing segments 2 and 3, projections 9 (and 9a) which are extensions of the segments of the housing, and opening 12 (and 12a). Guide elements 6 and 7 in FIG. 1A are shown guiding detached backing film 11 and mesh 10a at opening 12. FIG. 1B shows dispenser 1a having guide element 7 between projections 9a at opening 12a. Optional gripping means 27 and 28 may provide for user control. Optional indicia 25 may provide for indication of the forward direction. FIGS. 2 and 3 are an exploded view of the mesh dispenser 1 showing housing segment 3 separated therefrom for purposes of depicting the path of mesh, backing film, and mesh and backing film through the device and a plan view depicting the same elements, respectively. Thus, supply spool 4, rotatably mounted on supply spool axle 40b, with mesh and backing film 10 loaded thereon is rotatably coupled to take-up spool 13, rotatably mounted on take-up spool axle 40a. Mesh and backing film 10 is received by guide element 5 as it pays out from supply spool 4 and is then routed between guide elements 6 and 7 mounted at opening 12 on projections 9. Detached backing film 11 is received by guide element 8 and directed to take-up spool 13. Mesh 10a is dispensed via opening 12 with mesh bottom surface 21 having PSA presented to tissue or wound site. As depicted in FIGS. 2-3, the mesh dispenser comprises hand leader 30 attached to the beginning of the mesh at the outer wrap of supply spool 4 (such that the mesh may be protected and/or attached to the backing film within the interior of the dispenser prior to use). Hand leader follows the mesh-dispensing path out of the dispenser (e.g., around guide element 7) and may be attached to the exterior of the housing segments. To start mesh application, the end of hand leader 30 is freed from the housing and pulled towards the rear of mesh dispenser 1. The hand leader pulls mesh 10a from the backing film 11 and routes mesh 10a around guide element 7 to present mesh bottom surface 21 having PSA to tissue or wound site.

Figure 4:
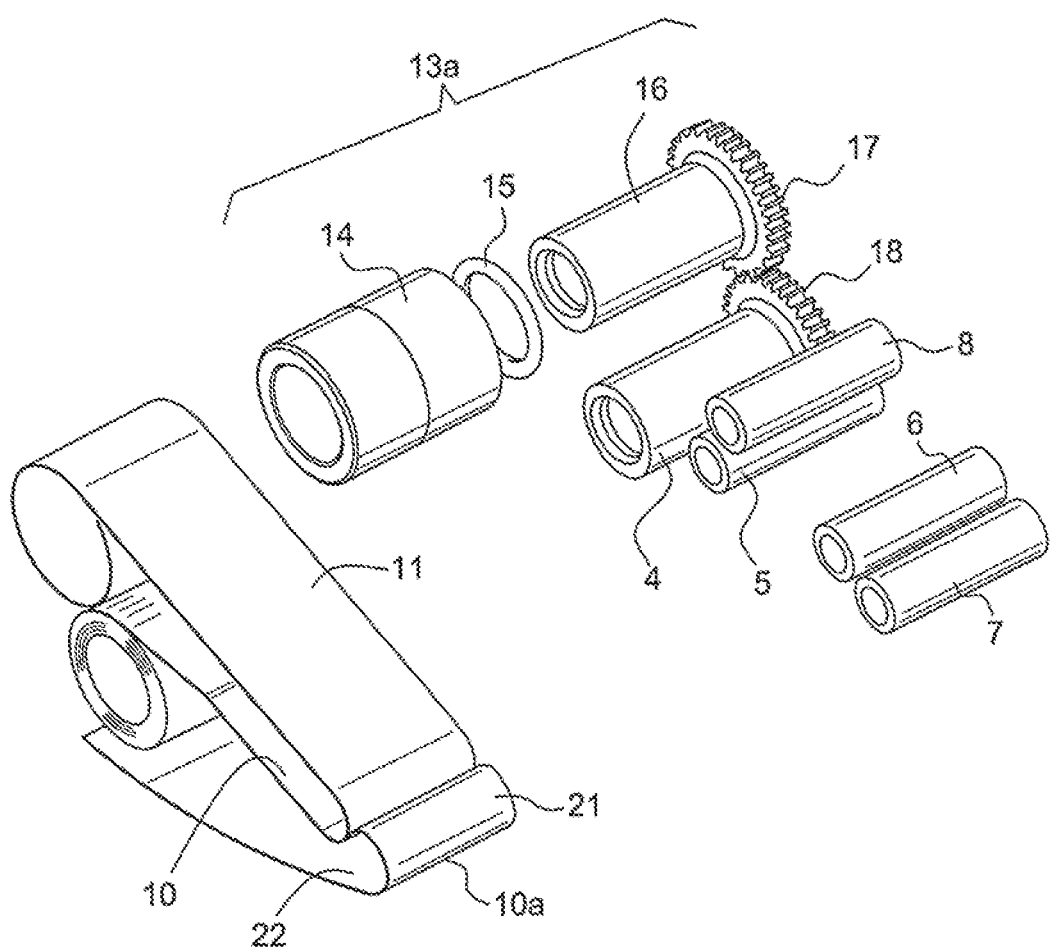
FIG. 4 is an exploded view of the embodiment of FIG. 1A.

FIG. 4 is an exploded view of the mesh dispenser embodiment of FIG. 1A, depicting means for elements of take-up spool assembly 13a, comprising take-up spool 16, take-up spool 16 having take-up spur gears 17 coupled with supply spur gears 18 of supply spool 4. Take up spool assembly 13a includes clutch elements including take-up sleeve 14 and o-ring 15 providing interference with take-up spool 16. Mesh and backing film 10 are shown as detached backing film 11, mesh bottom surface 21 having PSA, and mesh top layer 22 when separated.

During use of the mesh dispenser device herein disclosed, the adhesive side of the mesh is presented to the wound site and the device is pushed or pulled forward, for example, in the direction of indicia 25, along the wound line. After separating from backing film 11, mesh 10a passes over guide element 7 and bottom surface 21 is applied to the patient's skin. After separation from mesh and backing film 10, detached backing film 11 is routed past guide element 8 to take-up spool 13.

The present mesh dispenser may be modified without departing from the spirit and scope of the present mesh dispenser. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims.

We claim:
1. A flexible material dispensing device comprising:
a housing having an opening;
a supply spool rotatably mounted in the housing, the supply spool comprising a spool of flexible material and backing film, the flexible material comprising an adhesive substance applied over at least a portion of a side of the flexible material, and the backing film detachably adhered to the adhesive substance;
at least one guide element mounted in the housing, the at least one guide element receiving the flexible material and backing film from the supply spool, such that the adhesive side of the flexible material is presented at the opening of the housing;
a take-up spool rotatably mounted in the housing, the take-up spool rotatably coupled with the supply spool for receiving the detached backing film; and
means for reducing or eliminating binding or slack of the detached backing film as the flexible material is dispensed, wherein the means for reducing or eliminating binding or slack of the detached backing film comprises a backing film tensioner, the backing film tensioner comprising
a spring secured to the housing at one end of the spring;
a lever, the lever pivotally secured to the housing at one end of the lever; and
a tensioning element secured to an opposite end of the spring and an opposite end of the lever, the tensioning element positioned such that the take-up spool is between the tensioning element and the opening in the housing, the tensioning element receiving the backing film prior to the take-up spool.

* * * * *